(12) United States Patent
Su et al.

(10) Patent No.: US 7,744,816 B2
(45) Date of Patent: *Jun. 29, 2010

(54) METHODS AND DEVICE FOR BIOMOLECULE CHARACTERIZATION

(75) Inventors: Xing Su, Cupertino, CA (US); Andrew A. Berlin, San Jose, CA (US)

(73) Assignee: Intel Corporation, Santa Clara, CA (US)

( * ) Notice: Subject to any disclaimer, the term of this patent is extended or adjusted under 35 U.S.C. 154(b) by 728 days.

This patent is subject to a terminal disclaimer.

(21) Appl. No.: 10/138,157

(22) Filed: May 1, 2002

(65) Prior Publication Data

US 2003/0207326 A1    Nov. 6, 2003

(51) Int. Cl.
*G01N 33/48* (2006.01)
(52) U.S. Cl. ............... 422/68.1; 422/82.01; 422/82.11; 436/149
(58) Field of Classification Search ............... 422/58, 422/61, 99, 102, 104, 68.1, 82.01, 82.11; 436/164, 166, 149
See application file for complete search history.

(56) References Cited

U.S. PATENT DOCUMENTS

| | | |
|---|---|---|
| 4,962,037 A | 10/1990 | Jett et al. |
| 5,306,403 A | 4/1994 | Vo-Dinh |
| 5,324,637 A | 6/1994 | Thompson et al. |
| 5,332,666 A | 7/1994 | Prober et al. |
| 5,405,747 A | 4/1995 | Jett et al. |
| 5,436,130 A | 7/1995 | Mathies et al. |
| 5,721,102 A | 2/1998 | Vo-Dinh |
| 5,776,674 A | 7/1998 | Ulmer |

(Continued)

FOREIGN PATENT DOCUMENTS

WO     99/50654     * 10/1999

(Continued)

OTHER PUBLICATIONS

Lillo, et al., 1997. "Design and Characterization of a Multisite Fluorescence Energy-Transfer System for Protein Folding Studies: A Steady-State and Time-Resolved Study of Yeast Phoshpglycerate Kinase". Biochemistry 36: 11261-11272.

(Continued)

*Primary Examiner*—Lyle A Alexander
(74) *Attorney, Agent, or Firm*—Pillsbury Winthrop Shaw Pittman LLP

(57) ABSTRACT

The methods and apparatus 100, disclosed herein are of use for sequencing 150 and/or identifying 160 proteins 230, 310, polypeptides 230, 310 or peptides 230, 310. Proteins 230, 310 containing labeled amino acid residues may be synthesized and passed through nanopores 255, 330. A detector 257, 345 operably coupled to a nanopore 255, 330 may detect labeled amino acid residues as they pass through the nanopore 255, 330. Distance maps 140 for each type of labeled amino acid residue may be compiled. The distance maps 140 may be used to sequence 150 and/or identify 160 the protein 230, 310. In different embodiments of the invention, amino acid residues labeled with luminescent labels 235, 245 or nanoparticles 315 may be detected using photodetectors 257 or electrical detectors 345. Apparatus 100 of use for protein 230, 310 sequencing 150 and/or identification 160 are also disclosed herein.

34 Claims, 3 Drawing Sheets

U.S. PATENT DOCUMENTS

| | | |
|---|---|---|
| 5,783,389 A | 7/1998 | Vo-Dinh |
| 5,814,516 A | 9/1998 | Vo-Dinh |
| 5,821,058 A | 10/1998 | Smith et al. |
| 5,866,336 A | 2/1999 | Nazarenko et al. |
| 6,002,471 A | 12/1999 | Quake |
| 6,146,227 A | 11/2000 | Mancevski |
| 6,174,677 B1 | 1/2001 | Vo-Dinh |
| 6,210,896 B1 | 4/2001 | Chan |
| 6,355,420 B1 | 3/2002 | Chan |
| 2003/0059822 A1 | 3/2003 | Chan et al. |

FOREIGN PATENT DOCUMENTS

| | | |
|---|---|---|
| WO | 0125794 | 4/2001 |
| WO | 03078649 | 9/2003 |
| WO | 03106620 | 12/2003 |

OTHER PUBLICATIONS

Fisher, et al., 1999. "Lipid Induced Conformational Changes in the N-Terminal Domain of Human Apolipoprotein E". Journal of Lipid Research 40: 93-99.

* cited by examiner

US 7,744,816 B2

METHODS AND DEVICE FOR BIOMOLECULE CHARACTERIZATION

BACKGROUND OF THE INVENTION

1. Field of the Invention

The present invention relates to the fields of molecular biology and analysis of biomolecules including, but not limited to, proteins, polypeptides, peptides, lipids and polysaccharides. In particular, the invention relates to methods and apparatus for protein, polypeptide and/or peptide identification and/or sequencing.

2. Related Art

Identification and/or sequencing of biomolecules, such as proteins, are critical for medical diagnostics, forensics, toxicology, pathology, biological warfare, public health and numerous other fields. The ability to identify a particular pathogen or agent may depend on identification of one or more specific biomolecules characteristic of that pathogen or agent. Identification of regulatory pathways involved in disease processes, metabolism, growth and cell division may depend on identification and/or sequencing of biomolecules. Although a great deal of research is presently directed towards identification and/or sequencing of nucleic acids or proteins, other biomolecules such as carbohydrates, polysaccharides, lipids, fatty acids, etc. may be of importance. The methods and apparatus disclosed herein are focused on identification and/or sequencing of proteins, polypeptides and peptides. However, they are also of use for analysis of other types of biomolecules.

Existing methods for protein sequencing, based on the Edman degradation technique, are limited by the length of the protein that can be sequenced. Accurate sequence determination is limited to about 50 to 100 amino acid residues per sequencing run. Sequencing of longer proteins, which may be thousands of amino acid residues in length, requires cleavage into smaller fragments and assembly of overlapping short sequences. The process is laborious, expensive, inefficient and time-consuming and typically requires the use of radioactive labels and other hazardous chemicals, which can pose safety and waste disposal problems.

A variety of techniques are available for identification of proteins, polypeptides and peptides. Commonly, these involve binding and detection of antibodies that can recognize one or more epitopic domains on the protein. Although antibody-based identification of proteins is fairly rapid, such assays may occasionally show unacceptably high levels of false positive or false negative results, due to cross-reactivity of the antibody with different antigens, low antigenicity of the target analyte (leading to low sensitivity of the assay), non-specific binding of antibody to various surfaces, etc. They also require the preparation of antibodies that can recognize an individual protein or peptide. As such, they are not suitable for the identification of novel proteins that have not previously been characterized. More recently, mass spectroscopy has been used for peptide identification and/or sequencing. Proteins and polypeptides may be cleaved into smaller fragments and the amino acid composition of the fragments may be identified by mass spectroscopy. Analysis of a sufficient number of overlapping fragments can provide data on amino acid sequence. This process is also laborious, expensive and requires substantial preparation of the protein or peptide to be analyzed.

A need exists in the art for methods and apparatus suitable for the identification and/or sequencing of biomolecules, including proteins and peptides that have not previously been identified or characterized.

BRIEF DESCRIPTION OF THE DRAWINGS

The following drawings form part of the specification and are included to further demonstrate certain embodiments of the invention. The embodiments may be better understood by reference to one or more of these drawings in combination with the detailed description presented herein.

DETAILED DESCRIPTION OF THE INVENTION

Definitions

Figure 1:
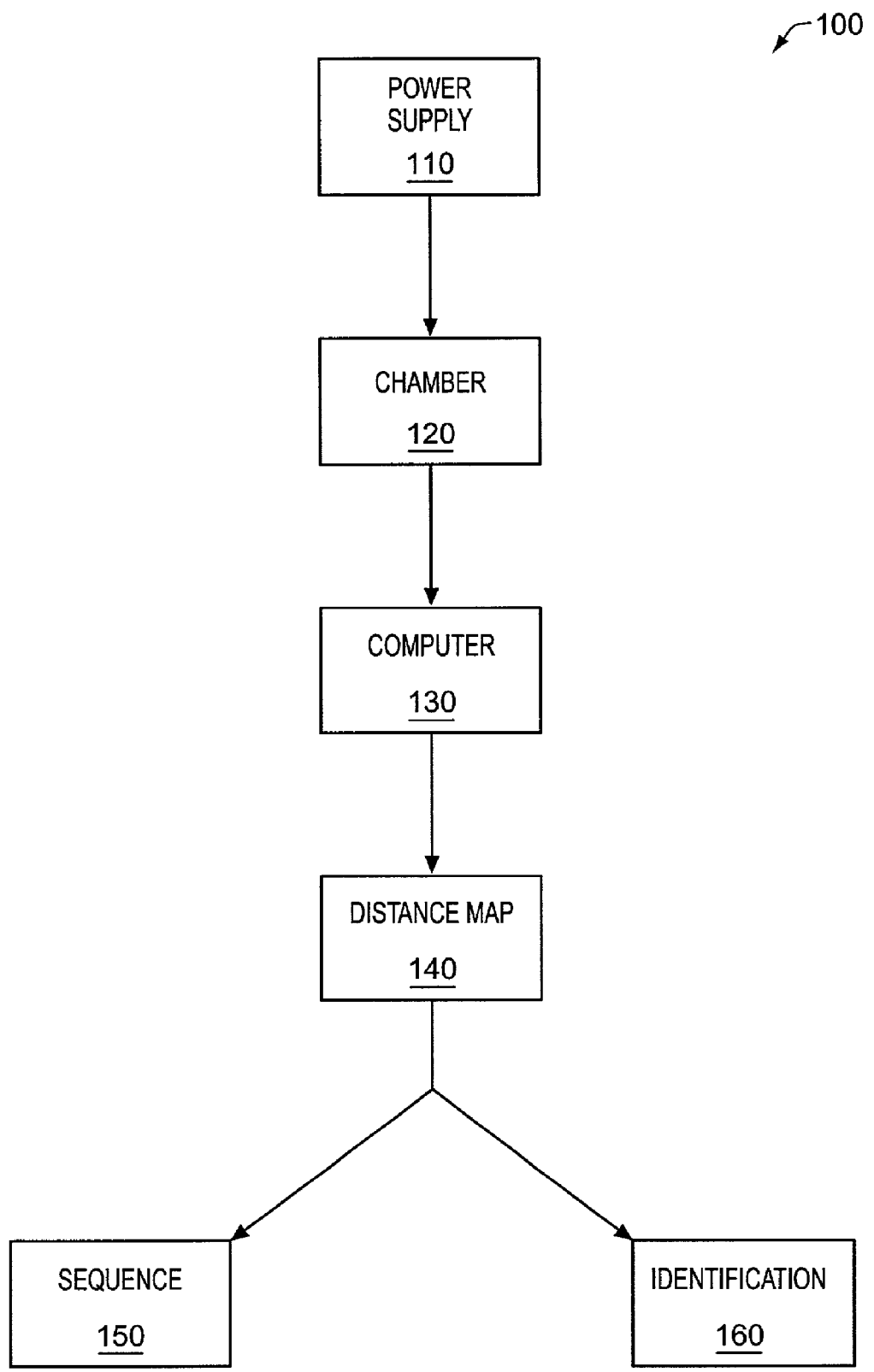
FIG. 1 is a flow chart illustrating a non-limiting exemplary apparatus 100 (not to scale) and methods for protein 230, 310 sequencing 150 and/or identification 160 by generation of distance maps 140.

As used herein, "a" or "an" may mean one or more than one of an item.

The terms "protein," 230, 310 "polypeptide" 230, 310 and "peptide" 230, 310 refer to polymeric molecules assembled in linear fashion from amino acids. The distinction between the terms is primarily one of length, with peptides 230, 310 typically ranging from about 2 to about 25 amino acid residues, polypeptides 230, 310 from about 10 to about 100 amino acid residues and proteins 230, 310 about 50 residues or longer. The terms overlap and the skilled artisan will realize that where the following disclosure refers to proteins 230, 310 or polypeptides 230, 310 or peptides 230, 310, the terms encompass polymers of any length comprising amino acid residues. Within the scope of the embodiments of the invention, it is contemplated that proteins 230, 310, polypeptides 230, 310 and peptides 230, 310 may comprise naturally occurring amino acid residues, modified amino acid residues, derivatized amino acid residues, amino acid analogues and/or non-naturally occurring amino acids. Amino acid residues that have been labeled with any labels 235, 245, 315 are also encompassed. Although amino acid residues in naturally occurring proteins 230, 310, polypeptides 230, 310 and peptides 230, 310 are typically joined together by peptide bonds, within the scope of the disclosed methods amino acid residues may be joined by peptide bonds or by any other type of known covalent attachment.

The terms "nanopore" 255, 330, "nanochannel" 255, 330 and "nanotube" 255, 330 refer respectively to a hole, channel or tube with a diameter or width of between 1 and 999 nanometers (nm), more typically between 1 and 100 nm, even more typically between 1 and 10 nm.

As used herein, "operably coupled" means that there is a functional interaction between two or more units. For example, a detector 257, 345 may be "operably coupled" to a nanopore 255, 330 if the detector 257, 345 is arranged so that it may identify labeled amino acid residues passing through the nanopore 255, 330. Similarly, a nanopore 255, 330 may be operably coupled to a chamber 120, 280, 290, 350, 360 if proteins 230, 310 in the chamber 120, 280, 290, 350, 360 can pass through the nanopore 255, 330.

As used herein, "fluid communication" refers to a functional connection between two or more compartments that allows fluids to pass between the compartments. For example, a first compartment is in "fluid communication" with a second compartment if fluid may pass from the first compartment to the second and/or from the second compartment to the first compartment.

DESCRIPTION OF ILLUSTRATIVE EMBODIMENTS

The disclosed methods and apparatus 100 are of use for the rapid, automated sequencing 150 and/or identification 160 of proteins 230, 310. Advantages over prior art methods include high throughput, sensitive detection of single labeled protein molecules 230, 310, nanometer scale resolution of amino acid residue distances and lower unit cost of protein 230, 310 sequencing 150 and/or identification 160.

The following detailed description contains numerous specific details in order to provide a more thorough understanding of the disclosed embodiments of the invention. However, it will be apparent to those skilled in the art that the embodiments of the invention may be practiced without these specific details. In other instances, devices, methods, procedures, and individual components that are well known in the art have not been described in detail herein.

Figure 2:
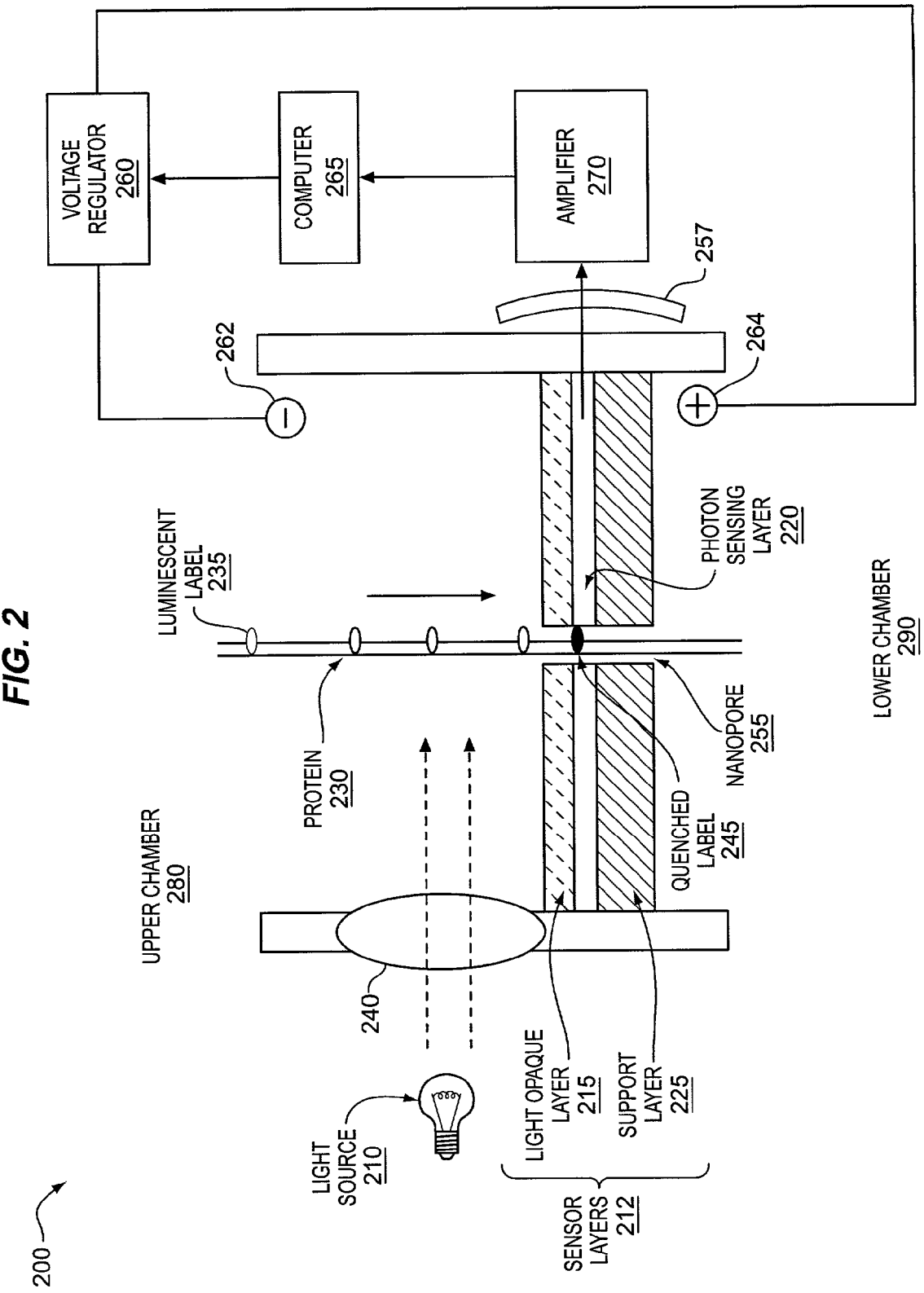
FIG. 2 illustrates a non-limiting example of an sub-device 200 (not to scale) for protein 230, 310 sequencing 150 and/or identification 160 by detection of luminescence.
Figure 3:
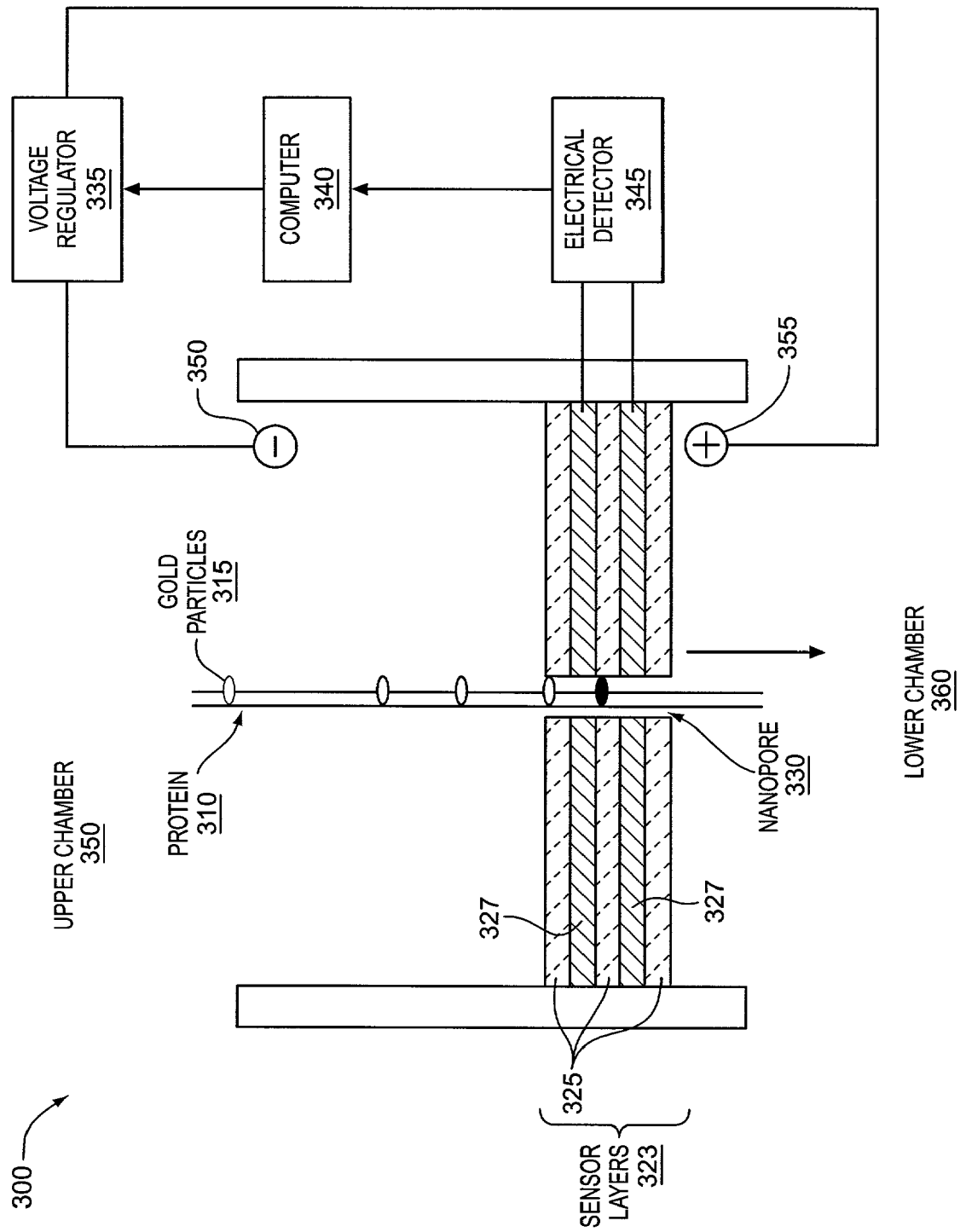
FIG. 3 illustrates another non-limiting example of an sub-device 300 (not to scale) for protein 230, 310 sequencing 150 and/or identification 160 by detection of electrical changes.

In certain embodiments of the invention, exemplified in FIG. 1 through FIG. 3, polymers such as proteins 230, 310, polypeptides 230, 310 and peptides 230, 310 may be identified 160 and/or sequenced 150 using the disclosed methods and apparatus 100. In exemplary embodiments of the invention illustrated in FIG. 1, a nucleic acid template is placed in one or more chambers 120, 280, 350, each chamber 120, 280, 350 to contain a different labeled amino acid. Labeled proteins 230, 310 encoded by the nucleic acid template are produced by in vitro translation or by linked transcription/translation. The labeled proteins 230, 310 pass through one or more nanopores 255, 330 associated with each chamber 120, 280, 350, the nanopores 255, 330 permeating one or more sensor layers 212, 323 operably coupled to a detector 257, 345. As a labeled protein 230, 310 passes through a nanopore 255, 330, labeled amino acid residues are detected. The distances between labeled amino acid residues are determined and a distance map 140 is compiled for each type of labeled amino acid residue. The distance maps 140 can be used to identify 160 the labeled protein 230, 310. In alternative embodiments of the invention, labeled proteins 230, 310 may be prepared by incubating cells in, for example, a labeled amino acid and purifying one or more proteins 230, 310 from the incubated cells. In other alternative embodiments, the cells may be transformed with an expression vector encoding a protein 230, 310 of interest. In certain embodiments of the invention where twenty chambers 120, 280, 350 contain twenty different labeled amino acid residues, the distance maps 140 can be compiled into a complete protein 230, 310 sequence 150.

Proteins, Polypeptides and Peptides

In different embodiments of the invention, proteins 230, 310 to be identified 160 and/or sequenced 150 may be: [1] purified from natural sources; [2] expressed by in vitro translation of an mRNA species or by linked transcription/translation of a DNA species; and/or [3] expressed in a host cell that has been transformed with a gene or a complementary DNA (cDNA) species. These methods are not limiting and proteins 230, 310 to be identified 160 and/or sequenced 150 may be prepared by any method known in the art.

Protein Purification

In certain embodiments of the invention, proteins 230, 310 to be identified 160 and/or sequenced 150 may be partially or fully purified from a variety of sources before analysis. Protein 230, 310 purification techniques are well known to those of skill in the art. These techniques typically involve an initial crude fractionation of cell or tissue homogenates and/or extracts into protein 230, 310 and non-protein fractions. Fractionation may utilize, for example, differential solubility in aqueous solutions, detergents and/or organic solvents, elimination of classes of contaminants such as nucleic acids by enzymatic digestion, precipitation of proteins 230, 310 with ammonium sulphate, polyethylene glycol, antibodies, heat denaturation and the like, followed by ultracentrifugation. Low molecular weight contaminants may be removed by dialysis, filtration and/or organic phase extraction.

Protein(s) 230, 310 of interest may be purified using chromatographic and/or electrophoretic techniques to achieve partial or complete purification. Methods suited to the purification of proteins 230, 310, polypeptides 230, 310 and peptides 230, 310 include, but are not limited to, ion-exchange chromatography, gel exclusion chromatography, polyacrylamide gel electrophoresis, affinity chromatography, immunoaffinity chromatography, hydroxylapatite chromatography, hydrophobic interaction chromatography, reverse phase chromatography, isoelectric focusing, fast protein liquid chromatography (FPLC) and high pressure liquid chromatography (HPLC). These and other methods of protein 230, 310 purification are known in the art and are not limiting for the claimed subject matter. Any known method of protein 230, 310 purification may be used. There is no requirement that the protein 230, 310 must be in its most purified state. Methods exhibiting a lower degree of relative purification may, for example, have advantages in increased recovery of labeled protein 230, 310.

Particular embodiments of the invention may rely on affinity chromatography for purification of proteins 230, 310. The method relies on an affinity between a protein 230, 310 and a molecule to which it can specifically bind. Chromatography material may be prepared by covalently attaching a protein-binding ligand, such as an antibody, antibody fragment, receptor protein, substrate, inhibitor, product or an analog of such ligands to an insoluble matrix, such as column chromatography beads or a nylon or other membrane. The matrix is then able to specifically adsorb the target protein 230, 310 from a solution. Elution occurs by changing the solvent conditions (e.g. pH, ionic strength, temperature, detergent concentration, etc.). One of the most common forms of affinity chromatography is immunoaffinity chromatography. Methods for generating antibodies against various types of proteins 230, 310 for use in immunoaffinity chromatography are well known in the art.

In some embodiments of the invention, one or more proteins 230, 310 of interest may be specifically labeled in order to facilitate purification. The protein 230, 310 of interest may be followed through a purification protocol by looking for the presence of labeled protein 230, 310. In other embodiments of the invention, proteins may be post-translationally labeled using side chain specific and/or selective reagents as discussed below. Various methods for protein 230, 310 labeling are known in the art, discussed in more detail below.

In Vitro Translation

Proteins 230, 310 may be expressed using an in vitro translation system with mRNA templates. Complete kits for performing in vitro translation are available from commercial sources, such as Ambion (Austin, Tex.), Promega (Madison, Wis.), Amersham Pharmacia Biotech (Piscataway, N.J.), Invitrogen (Carlsbad, Calif.) and Novagen (Madison, Wis.). Such kits may utilize total RNA, purified polyadenylated mRNA, and/or purified individual mRNA species obtained from a cell, tissue or other sample. Methods of preparing different RNA fractions and/or individual mRNA species for use in in vitro translation are known. (E.g., Sambrook, et al., Molecular Cloning: A Laboratory Manual, Cold Spring Harbor Laboratory Press, Cold Spring Harbor, N.Y., 1989; Ausubel et al., Current Protocols in Molecular Biology, Wiley and Sons, New York, N.Y., 1994).

Commonly used in vitro translation systems are based on rabbit reticulocyte lysates, wheat germ extracts and E. coli extracts. In vitro translation systems based on rabbit reticulocyte lysates are particularly robust and efficient for eukaryotic translation. The systems contain crude cell extracts including ribosomal subunits, transfer RNAs (tRNAs), aminoacyl-tRNA synthetases, initiation, elongation and termination factors and/or all other components required for translation. In certain embodiments of the invention, the natural amino acids present in such extracts may be supplemented with one or more different types of labeled amino acids. Depending on the embodiment, the label 235, 245, 315 may be restricted to a single type of amino acid. Alternatively, a sample to be translated may be divided up into different sub-samples, each of which may be exposed to a different type of labeled amino acid. Other components of use in supplementing in vitro translation systems and methods of use of such systems are known in the art (e.g., www.ambion-.com/basics/translation/translation101.html).

In certain alternative embodiments of the invention, in vitro translation may be linked to transcription of genes to generate mRNAs. Such linked transcription/translation systems may use PCR® amplification products and/or DNA sequences inserted into standard expression vectors such as BACs (bacterial artificial chromosomes), YACs (yeast artificial chromosomes), cosmids, plasmids, phage and/or other known expression vectors. Linked transcription/translation systems are available from commercial sources (e.g., Proteinscript™ II kit, Ambion, Austin, Tex.; Quick Coupled System, Promega, Madison, Wis.; Expressway, Invitrogen, Carlsbad, Calif.). Such systems may incorporate various elements to optimize the efficiency of transcription and translation, such as polyadenylation sequences, consensus ribosomal binding (Kozak) sequences, Shine-Dalgarno sequences and/or other regulatory sequences known in the art.

In different embodiments of the invention, labeled proteins 230, 310 may be purified from the crude in vitro translation mixture prior to analysis by the disclosed methods and apparatus 100, or alternatively may be analyzed without purification. The use of protein 230, 310 purification may depend in part on whether a crude RNA fraction or a purified RNA species is used as the template for translation.

Protein Expression in Host Cells

Nucleic acids encoding target proteins 230, 310 of interest may be incorporated into expression vectors for transformation into host cells and production of the encoded proteins 230, 310. Non-limiting examples of host cell lines known in the art include bacteria such as E. coli, yeast such as Pichia pastoris, and mammalian cell lines such as VERO cells, HeLa cells, Chinese hamster ovary cell lines, human embryonic kidney (HEK) 293 cells, mouse neuroblastoma N2A cells, or the W138, BHK, COS-1, COS-7, 293, HepG2, 3T3, RIN, L-929 and MDCK cell lines. These and other host cell lines may be obtained from standard sources, such as the American Type Culture Collection (Rockville, Md.) or commercial vendors.

A complete gene can be expressed or fragments of a gene encoding portions of a protein 230, 310 can be expressed. The gene or gene fragment encoding protein(s) 230, 310 of interest may be inserted into an expression vector by standard cloning techniques. Expression libraries containing part or all of the messenger RNAs expressed in a given cell or tissue type may be prepared by known techniques. Such libraries may be screened for clones encoding particular proteins 230, 310 of interest, for example using antibody or oligonucleotide probes and known screening techniques.

The engineering of DNA segment(s) for expression in a prokaryotic or eukaryotic system may be performed by techniques generally known in the art. Any known expression system may be employed for protein 230, 310 expression. Expression vectors may comprise various known regulatory elements for protein 230, 310 expression, such as promoters, enhancers, ribosome binding sites, termination sequences, polyadenylation sites, etc.

Promoters commonly used in bacterial expression vectors include the β-lactamase, lactose and tryptophan promoter systems. Suitable promoter sequences in yeast expression vectors include the promoters for 3-phosphoglycerate kinase or other glycolytic enzymes. Promoters of use for mammalian cell expression may be derived from the genome of mammalian cells (e.g., metallothionein promoter) or from mammalian viruses (e.g., the adenovirus late promoter or the early and late promoters of SV40). Many other promoters are known and may be used in the practice of the disclosed methods.

Eukaryotic expression systems of use include, but are not limited to, insect cell systems infected with, for example, recombinant baculovirus, or plant cell systems infected with recombinant cauliflower mosaic virus or tobacco mosaic virus. In an exemplary insect cell system, Autographa californica nuclear polyhidrosis virus is used as a vector to express foreign genes in Spodoptera frugiperda cells or the Hi5 cell line (Invitrogen, Carlsbad, Calif.). Nucleic acid coding sequences are cloned into, for example, the polyhedrin gene of the virus under control of the polyhedrin promoter. Recombinant viruses containing the cloned gene are then used to infect Spodoptera frugiperda cells and the inserted gene is expressed (e.g., U.S. Pat. No. 4,215,051; Kitts et al., Biotechniques 14:810-817, 1993; Lucklow et al., J. Virol., 67:4566-79, 1993). Other exemplary insect cell expression vectors are based on baculovirus vectors, for example, pBlue-Bac (Invitrogen, Sorrento, Calif.).

An exemplary expression system in mammalian cell lines may utilize adenovirus as an expression vector. Coding sequences may be ligated to, e.g., the adenovirus late promoter. The cloned gene may be inserted into the adenovirus genome by in vitro or in vivo recombination. Insertion in a non-essential region of the viral genome (e.g., region E1 or E3) results in a recombinant virus that is capable of infecting and expressing cloned proteins 230, 310 in mammalian host cells. The disclosed examples are not limiting and any known expression vector may be used.

In certain embodiments of the invention, cells transformed with expression vectors may be selected from non-transformed cells. A number of selection systems may be used, including but not limited to, the thymidine kinase gene, hypoxanthine-guanine phosphoribosyltransferase gene, methotrexate resistance gene, neomycin phosphotransferase gene and hygromycin resistance gene. These genes, contained in standard cloning vectors, either confer resistance to cytotoxic agents or allow cell growth in nutrient deficient medium.

Expressed proteins 230, 310 may be partially or completely purified before analysis. In some embodiments of the invention, protein 230, 310 purification may be facilitated by expressing cloned sequences as fusion proteins 230, 310 containing short leader sequences that allow rapid affinity purification. Examples of such fusion protein 230, 310 expression systems are the glutathione S-transferase system (Pharmacia, Piscataway, N.J.), the maltose binding protein system (NEB, Beverley, Mass.), the FLAG system (IBI, New Haven, Conn.), and the 6xHis system (Qiagen, Chatsworth, Calif.). In one embodiment of the invention, the leader sequence is linked to a protein 230, 310 by a specific recognition site for a protease. Examples of suitable sequences include those recognized by the Tobacco Etch Virus protease (Life Technologies, Gaithersburg, Md.) or Factor Xa (New England Biolabs, Beverley, Mass.). Alternatively, expressed proteins 230, 310 may be purified by standard techniques discussed above.

Although the methods disclosed above are directed towards identification 160 and/or sequencing 150 of proteins 230, 310, they are also applicable to the identification 160 and/or sequencing 150 of other types of biomolecules. For example, cells could be incubated in a labeled monosaccharide and polysaccharides could be purified and identified 160 and/or sequenced 150 as described herein. In certain embodiments of the invention, the labeled subunit (e.g., monosaccharide) may be derivatized to prevent its metabolism and conversion to a different structure. Subunits and polymeric forms of biomolecules are known in the art.

Protein Labeling

In various embodiments of the invention, proteins 230, 310 may comprise labeled amino acid residues. Amino acids may be labeled by any methods known in the art. In certain embodiments, a labeled amino acid residue may be incorporated into a protein 230, 310 during synthesis. In other embodiments of the invention, labels 235, 245, 315 may be attached to amino acid residues by covalent or non-covalent bonding after protein 230, 310 synthesis.

Labels 235, 245, 315 of use in the disclosed methods may include, but are not limited to, any composition detectable by electrical, optical, spectrophotometric, photochemical, biochemical, immunochemical, and/or chemical techniques. Labels 235, 245, 315 may include, but are not limited to, conducting, luminescent, fluorescent, chemiluminescent, bioluminescent and phosphorescent labels, nanoparticles, metal nanoparticles, gold nanoparticles, silver nanoparticles, chromogens, antibodies, antibody fragments, genetically engineered antibodies, enzymes, substrates, cofactors, inhibitors, binding proteins, magnetic particles and spin labels.

Non-limiting examples of photodetectable labels 235, 245 that may be used include dansyl chloride, rhodamine isothiocyanate, TRIT (tetramethyl rhodamine isothiol), NBD (7-nitrobenz-2-oxa-1,3-diazole), Texas Red, phthalic acid, terephthalic acid, isophthalic acid, cresyl fast violet, cresyl blue violet, brilliant cresyl blue, para-aminobenzoic acid, erythrosine, biotin, digoxigenin, fluorescein, 5-carboxy-4',5'-dichloro-2',7'-dimethoxy fluorescein, 5-carboxy-2',4',5',7'-tetrachlorofluorescein, 5-carboxyfluorescein, 5-carboxyrhodamine, aminoacridine, 6-carboxyrhodamine, 6-carboxytetramethyl amino phthalocyanines, azomethines, cyanines, xanthines, succinylfluoresceins, rare earth metal cryptates, europium trisbipyridine diamine, a europium cryptate or chelate, diamine, dicyanins, La Jolla blue dye, allopycocyanin, allococyanin B, phycocyanin C, phycocyanin R, thiamine, phycoerythrocyanin, phycoerythrin R, luciferin, or acridinium esters. These and other luminescent labels 235, 245 may be obtained from commercial sources such as Molecular Probes (Eugene, Oreg.) and attached to amino acids by methods known in the art. Alternatively, certain pre-labeled amino acids are commercially available (e.g., Molecular Probes, Eugene, Oreg.).

In other embodiments of the invention, amino acid residues may be labeled with electrically detectable labels 315, such as metal nanoparticles 315. In various embodiments of the invention, gold or silver nanoparticles 315 of between 1 nm and 3 nm in size may be used, although nanoparticles 315 of different dimensions and mass may also be used. Methods of preparing nanoparticles 315 are known. (See e.g., U.S. Pat. Nos. 6,054,495; 6,127,120; 6,149,868; Lee and Meisel, *J. Phys. Chem.* 86:3391-3395, 1982.) Nanoparticles 315 may also be obtained from commercial sources (e.g., Nanoprobes Inc., Yaphank, N.Y.; Polysciences, Inc., Warrington, Pa.). Modified nanoparticles 315 are available commercially, such as Nanogold® nanoparticles 315 from Nanoprobes, Inc. (Yaphank, N.Y.). Nanogold® nanoparticles 315 may be obtained with either single or multiple maleimide, amine or other groups attached per nanoparticle 315. The Nanogold® nanoparticles 315 also are available in either positively or negatively charged form. Such modified nanoparticles 315 may be attached covalently to amino acid residues either before or after the amino acid residues are incorporated into proteins 230, 310. In certain embodiments of the invention, nanoparticles 315 or other labels 235, 245, 315 may be attached to amino acid residues via any known linker compound to reduce steric hindrance and facilitate protein 230, 310 polymerization.

In certain embodiments of the invention, labeled amino acid residues may be incorporated into proteins 230, 310 made from a nucleic acid template. In other embodiments of the invention, labels 235, 245, 315 may be attached to a particular type of amino acid residue after synthesis of the protein 230, 310. In other embodiments of the invention, the label 235, 245, 315 may be attached by antibody-antigen interactions. In certain embodiments of the invention, a label 235, 245, 315 such as fluorescein or biotin may be attached to one end of a protein molecule 230, 310, such as the N-terminal or C-terminal end.

In some embodiments of the invention, proteins, polypeptides and/or peptides may be post-translationally labeled using side-chain specific and/or selective reagents. Such reagents and methods for post-translational modification are known in the art. Non-limiting exemplary reagents that may be used include acetic anhydride (lysine, cysteine, serine and tyrosine); trinitrobenzenesulfonate (lysine); carbodiimides (glutamate, aspartate); phenylglyoxal (arginine); 2,3-butanedione (arginine); pyridoxal phosphate (lysine); p-chloromercuribenzoate (cysteine); 5,5'-dithiobis(2-nitro-benzoic acid) (cysteine); diethylpyrocarbonate (lysine, histidine); N-bromosuccinimide (tryptophan) and tetranitromethane (cysteine, tyrosine). Such reagents may be modified to attach various types of labels, such as fluorescent labels. Alternatively, fluorescent labels and/or gold nanoparticles that contain reactive groups for attachment to various types of amino acid side chains may be obtained from commercial sources (Molecular Probes, Eugene, Oreg.; Nanoprobes, Inc., Yaphank, N.Y.).

In alternative embodiments of the invention, various cross-linking reagents known in the art, such as homo-bifunctional, hetero-bifunctional and/or photoactivatable cross-linking reagents may be used to attach labels to proteins, polypeptides and/or peptides. Non-limiting examples of such reagents include bisimidates; 1,5-difluoro-2,4-(dinitrobenzene); N-hydroxysuccinimide ester of suberic acid; disuccinimidyl tartarate; dimethyl-3,3'-dithiobispropionimidate; N-succinimidyl-3-(2-pyridyldithio)propionate; 4-(bromoaminoethyl)-2-nitrophenylazide; and 4-azidoglyoxal.

Nanopores, Nanochannels and Nanotubes

In certain embodiments of the invention, labeled proteins 230, 310 or other polymers may be passed through one or more nanopores 255, 330, nanochannels 255, 330 or nanotubes 255, 330 for analysis. In various embodiments of the invention, nanopores 255, 330, nanotubes 255, 330 and nanochannels 255, 330 may be used interchangeably. The skilled artisan will realize that where the specification refers to a nanopore 255, 330, different embodiments of the invention may use a nanochannel 255, 330 or nanotube 255, 330. The only requirement is that the nanopore 255, 330, nanochannel 255, 330 or nanotube 255, 330 connect one fluid filled compartment to another and allow the passage and detection of labeled proteins 230, 310.

Size Characteristics

In some embodiments of the invention, nanopores 255, 330 of use may be about 0.5, 1, 2, 3, 4, 5, 6, 7, 8, 9 or 10 nm in diameter. In other embodiments of the invention, the diameter may range between 1-3, 1-5, 1-10, 1-20, 1-50, 1-100, 5-10, 5-20, 10-20, 20-50, 30-75, 50-75, 50-100, 75-100, 100-300, 300-400, 400-500 or 100-999 nm. Nanopore 255, 330 diameter may be selected to pass a single protein 230, 310 at a time, in a linear configuration. In certain embodiments of the invention, nanopore 255, 330 diameter may be selected to be too small to pass a protein 230, 310 in a globular or folded conformation. The dimensions of various folded and unfolded proteins 230, 310 are known in the art. In particular embodiments of the invention, proteins 230, 310 may be unfolded and/or partially or fully denatured by known methods to facilitate their passage through a nanopore 255, 330 in a linear conformation. Such methods may include, but are not limited to, exposure to media of either alkaline or acidic pH, use of high or low salt concentrations, use of detergents such as sodium dodecyl sulphate, octylglucoside or Triton X-100, use of chaotrophic agents such as urea or guanidinium, treatment with disulfide reducing agents such as dithiothreitol or mercaptoethanol, exposure to organic solvents, etc. Alternatively, linear peptides may be generated by limited proteolytic digestion of proteins. In embodiments of the invention where the amino acid residues are labeled with bulky groups 235, 245, 315, the nanopores 255, 330 may be larger to allow passage of labeled proteins 230, 310. In alternative embodiments of the invention that utilize nanotubes 255, 330 or nanochannels 255, 330 in place of nanopores 255, 330, the same size considerations apply to the diameter or width of the nanotubes 255, 330 or nanochannels 255, 330.

Fabrication of Nanopores, Nanotubes and Nanochannels

Fabrication of nanopores 255, 330, nanotubes 255, 330 and/or nanochannels 255, 330, individually or in arrays, may utilize any technique known in the art for nanoscale manufacturing. In certain embodiments of the invention, nanopores 255, 330, nanochannels 255, 330 and/or nanotubes 255, 330 may be constructed on a solid-state matrix comprising sensor layers 212, 323 using known nanolithography methods, including but not limited to chemical vapor deposition, electrochemical deposition, chemical deposition, electroplating, thermal diffusion and evaporation, physical vapor deposition, sol-gel deposition, focused electron beam, focused ion beam, molecular beam epitaxy, dip-pen nanolithography, reactive-ion beam etching, chemically assisted ion beam etching, microwave assisted plasma etching, electro-oxidation, scanning probe methods, chemical etching, laser ablation, or any other method known in the art (E.g., U.S. Pat. No. 6,146,227).

In various embodiments of the invention, nanopores 255, 330 may penetrate one or more sensor layers 212, 323. The sensor layers 212, 323 may comprise semiconductor materials including, but not limited to, silicon, silicon dioxide, silicon nitride, germanium, gallinium arsenide, and/or metal-based compositions such as metals or metal oxides. In some embodiments of the invention, sensor layers 212, 323 may be processed by electronic beam, ion beam and/or laser lithography and etching to create a channel, groove, or hole. Conducting layers comprising metals may be deposited onto a semiconductor surface by means of field evaporation from a scanning tunnel microscope (STM) or atomic force microscope (AFM) tip or from a solution. Insulating layers 325 may be formed by oxidizing the semiconductor's surface to an insulating composition.

In certain embodiments of the invention, channels or grooves may be etched into a semiconductor surface by various techniques known in the art including, but not limited to, methodologies using an STM/AFM tip in an oxide etching solution. After channels are formed, two semiconductor surfaces may be opposed to create one or more nanopores 255, 330 or nanochannels 255, 330 that penetrate the semiconductor. In other embodiments of the invention, STM tip methodologies may be used to create nanopores 255, 330, nanodetectors 257, 345, nanowires, nanoleads, nanochannels 255, 330, and other nanostructures using techniques known in the art. In alternative embodiments of the invention, scanning probes, chemical etching techniques, and/or micromachining may be used to cut micrometer-dimensioned or nanometer-dimensioned channels, grooves or holes in a semiconductor substrate.

In certain embodiments of the invention, nano-molding may be employed, wherein formed nanotubes 255, 330, such as carbon or metallic nanotubes 255, 330, are placed or grown on a semiconductor chip substrate. After depositing additional material on the substrate, the nanotubes 255, 330 are removed, leaving a nanochannel 255, 330 and/or nanopore 255, 330 imprint in the substrate material. Such nanostructures can be built in clusters with properties of molecular electrodes that may function as detectors 257, 345.

In some embodiments of the invention, nanopores 255, 330 and/or nanochannels 255, 330 may be made using a high-throughput electron-beam lithography system (e.g., http://www.mdatechnology.net/techsearch.asp?articleid=510).

Electron-beam lithography may be used to write features as small as 5 nm on silicon chips. Sensitive resists, such as polymethylmethacrylate, coated on silicon surfaces may be patterned without use of a mask. The electron-beam array may combine a field emitter cluster with a microchannel amplifier to increase the stability of the electron beam, allowing operation at low currents. In some embodiments of the invention, the SoftMask™ control system may be used to control electron-beam lithography of nanoscale features on a semiconductor chip substrate.

In alternative embodiments of the invention, nanopores 255, 330 and/or nanochannels 255, 330 may be produced using focused atom lasers (e.g., Bloch et al., "Optics with an atom laser 210 beam," *Phys. Rev. Lett.* 87:123-321,1). Focused atom lasers may be used for lithography, much like standard lasers or focused electron beams. Such techniques are capable of producing micron scale or even nanoscale structures on a chip. In other alternative embodiments of the invention, dip-pen nanolithography may be used to form nanochannels 255, 330 (e.g., Ivanisevic et al., "Dip-Pen Nanolithography on Semiconductor Surfaces," *J. Am. Chem. Soc.*, 123: 7887-7889,1). Dip-pen nanolithograpy uses AFM techniques to deposit molecules on surfaces, such as silicon chips. Features as small as 15 nm in size may be formed, with spatial resolution of 10 nm. Nanoscale pores 255, 330 and/or channels 255, 330 may be formed by using dip-pen nanolithography in combination with regular photolithography techniques. For example, a micron scale line in a layer of resist may be formed by standard photolithography. Using dip-pen nanolithography, the width of the line and the corresponding diameter of the channel after etching may be narrowed by depositing additional resist compound. After etching of the thinner line, a nanoscale channel 255, 330 may be formed. Alternatively, AFM methods may be used to remove photoresist material to form nanometer scale features.

In other embodiments of the invention, ion-beam lithography may be used to create nanopores 255, 330 and/or nanochannels 255, 330 on a chip (e.g., Siegel, "Ion Beam Lithography," VLSI Electronics, Microstructure Science, Vol. 16, Einspruch and Watts Eds., Academic Press, New York, 1987). A finely focused ion beam may be used to write nanoscale features directly on a layer of resist without use of a mask. Alternatively, broad ion beams may be used in combination with masks to form features as small as 100 nm in scale. Chemical etching, for example, with hydrofluoric acid, is used to remove exposed silicon or other chip material that is not protected by resist. The skilled artisan will realize that the techniques disclosed above are not limiting, and that nanopores 255, 330 and/or nanochannels 255, 330 may be formed by any method known in the art.

In certain embodiments of the invention, the surfaces of nanopores 255, 330, nanotubes 255, 330 or nanochannels 255, 330 may be modified by coating, for example to transform a surface from a hydrophobic to a hydrophilic surface and/or to decrease adsorption of polymers such as proteins 230, 310 to a surface. Surface modification of common chip materials such as glass, silicon and/or quartz is known in the art (e.g., U.S. Pat. No. 6,263,286). Such modifications may include, but are not limited to, coating with commercially available capillary coatings (Supelco, Bellafonte, Pa.), silanes with various functional groups such as polyethyleneoxide or acrylamide, or any other known coating. Such coatings may not be appropriate where they would interfere with label 235, 245, 315 detection, such as interfering with electrical conductivity using an electrical detector 345.

Carbon Nanotubes

In some embodiments of the invention, nanopores 255, 330 may comprise, be attached to or be replaced by nanotubes 255, 330, such as carbon nanotubes 255, 330. In various embodiments of the invention, the carbon nanotubes 255, 330 may be coated with an organic or inorganic composition, leaving a deposited layer "mold" on the carbon nanotube 255, 330. When the nanotube 255, 330 is removed and separated from the organic or inorganic deposit, a nanopore 255, 330 may be created in the "mold." Carbon nanotubes 255, 330 may be formed in a semiconductor with other components, such as sensor layers 212, 323, formed around the nanotubes 255, 330.

In certain embodiments of the invention, carbon nanotubes 255, 330 may be manufactured by chemical vapor deposition (CVD), using ethylene and iron catalysts deposited on silicon (e.g., Cheung et al. PNAS 97:3809-3813, 2000). Single-wall carbon nanotubes 255, 330 may be formed on silicon chips by CVD using AFM $Si_3N_4$ tips (e.g., Cheung, et al., 2000; Wong, et al. Nature 394: 52-55, 1998; http://cmliris.harvard.edu/html_natlya/research/nanofabrication/nanofab.html). A flat surface of 1-5 $\mu m^2$ is created on the silicon AFM tips by contact with silicon or CVD diamond surfaces (GE Suprabrasives, Worthington, Ohio) at high load (~1 μN), at high scan speed (30 Hz), and with a large scan size (40 μm) for several minutes. Approximately 100 nm diameter, 1 μm deep pores in the ends of the AFM tips are made by anodization at 2.1 V for 100 sec. Anodized tips may be etched in 0.03% KOH in water for 50 sec, after which excess silicon is removed with ethanol, resulting in nanopores 255, 330 formed at the surface of the tip.

Carbon nanotubes 255, 330 may be attached to AFM tips using known methods. For example, iron catalyst consisting of iron oxide nanoparticles may be synthesized according to Murphy et al. (Austr. J. Soil Res. 13:189-201, 1975). Iron catalyst (0.5 to 4 nm particles) may be electrochemically deposited from a colloidal suspension into the pores using platinum counter electrodes at −0.5 V (Cheung, et al., 2000). Tips may be washed in water to remove excess iron oxide particles. AFM tips may be oxidized by heating in oxygen gas and carbon nanotubes 255, 330 may be grown on the catalyst by controlled heating and cooling in the presence of a carbon source (Murphy et al., 1975; Cheung et al., 2000). The diameter of the resulting nanotubes 255, 330 should correspond to the size of the iron oxide catalyst used (0.5 to 4 nm). Individual, single-walled nanotubes 255, 330 prepared under these conditions are aligned perpendicular to the flattened surface of the AFM tip. Residual iron catalyst may be removed by known methods.

Nanotubes 255, 330 may be cut to a predetermined length using known techniques. In some embodiments of the invention, carbon nanotubes 255, 330 may be attached to pyramids of gold-coated silicon cantilevers using an acrylic adhesive. The carbon nanotubes 255, 330 may be shortened to a defined length by application of a bias voltage between the tip and a niobium surface in an oxygen atmosphere (Wong, et al., Nature 394:52-55, 1998). In other embodiments of the invention, high-energy beams may be used to shorten carbon nanotubes 255, 330. Such high energy beams may include, but are not limited to, laser beams, ion beams, and electron beams. Alternative methods for truncating carbon nanotubes 255, 330 are known in the art (e.g., U.S. Pat. No. 6,283,812). In other embodiments of the invention, preformed carbon nanotubes 255, 330 may be attached to a chip material such as silicon, glass, ceramic, germanium, polystyrene, and/or gallium arsenide (e.g., U.S. Pat. Nos. 6,038,060 and 6,062,931).

In certain embodiments of the invention, a first set of carbon nanotubes 255, 330 may be used as cold cathode emitters on semiconductor chips, associated with a second set of nanotubes 255, 330 containing proteins 230, 310. The first set of nanotubes 255, 330 may be used to create local electrical fields of at least $10^6$ volts/cm, when an external voltage of between 10 and 50 volts is applied. Such an electric field in the first set of nanotubes 255, 330 can be used to drive proteins 230, 310 through the second set of nanotubes 255, 330, or to generate an electrical or electromagnetic signal to detect labeled amino acid residues (Chuang, et al., 2000; U.S. Pat. No. 6,062,931). In certain embodiments of the invention, electromagnetic radiation from a third set of nanotubes 255, 330 may excite a luminescent label 235, 245 attached to a protein 230, 310 passing through a second set of nanotubes 255, 330, leading to emission of light detected by a photodetector 257 that is operably coupled to a first set of nanotubes 255, 330.

Ion Channels on Semiconductor Chips

In some embodiments of the invention, nanopores 255, 330 may comprise single ion channels in lipid bilayer membranes (e.g., Kasianowitz, et al., Proc. Natl. Acad. Sci. USA 93:13770-13773, 1996). Such ion channels may include, but are not limited to, *Staphylococcus aureus* alpha-hemolysin and/or mitochondrial voltage-dependent anion channels. These ion channels may remain open for extended periods of time. An electric field applied to proteins 230, 310 can cause these molecules to move through ion channels in lipid bilayer membranes. Ion channels may be incorporated into chips and operably coupled to detectors 257, 345.

Micro-Electro-Mechanical Systems (MEMS)

In some embodiments of the invention, nanopores 255, 330, sensor layers 212, 323 and other components of the disclosed apparatus 100 may be incorporated into one or more Micro-Electro-Mechanical Systems (MEMS). MEMS are integrated systems that may comprise mechanical elements, actuator elements, control elements, detector 257, 345 elements and/or electronic elements. All of the components may be manufactured by known microfabrication techniques on a common chip, comprising a silicon-based or equivalent substrate (e.g., Voldman et al., Ann. Rev. Biomed. Eng. 1:401-425, 1999).

The electronic components of MEMS may be fabricated using integrated circuit (IC) processes (e.g., CMOS, Bipolar, or BICMOS processes). They may be patterned using photolithographic and etching methods known for semiconductor chip manufacture. The micromechanical components may be fabricated using "micromachining" processes that selectively etch away parts of the silicon wafer and/or add new structural layers to form the mechanical and/or electromechanical components. Basic techniques in MEMS manufacture include depositing thin films of material on a substrate, applying a patterned mask on top of the films by photolithographic imaging or other known lithographic methods, and selectively etching the films. A thin film may have a thickness in the range of a few nanometers to 100 micrometers. Deposition techniques of use may include chemical procedures such as chemical vapor deposition (CVD), electrodeposition, epitaxy and thermal oxidation and physical procedures like physical vapor deposition (PVD) and casting. Sensor layers 212, 323, of 5 nm thickness or less may be formed by such known techniques. Standard lithography techniques may be used to create sensor layers 212, 323 of micron or sub-micron dimensions, operably coupled to detectors 257, 345 and nanopores 255, 330.

The manufacturing method is not limiting and any methods known in the art may be used, such as atomic layer deposition, pulsed DC magnetron sputtering, vacuum evaporation, laser ablation, injection molding, molecular beam epitaxy, dip-pen nanolithograpy, reactive-ion beam etching, chemically assisted ion beam etching, microwave assisted plasma etching, focused ion beam milling, electron beam or focused ion beam technology or imprinting techniques. Methods for manufacture of nanoelectromechanical systems may be used for certain embodiments of the invention. (See, e.g., Craighead, Science 290:1532-36,0.)

In various embodiments of the invention, it is contemplated that some or all of the components of the apparatus 100 exemplified in FIG. 1 through FIG. 3 may be constructed as part of an integrated MEMS device. In certain embodiments of the invention, nanoelectrodes comprising conducting metals such as gold, platinum, or copper may be operably coupled to nanopores 255, 330, nanochannels 255, 330 and/or nanotubes 255, 330 using STM technologies known in the art (e.g., Kolb et al., Science 275:1697-1099, 1997). Nanoelectrodes, detectors 257, 345 and other components may be connected by nanowires.

Detectors

Electrical Detectors

In certain embodiments of the invention, a detector 345 may detect electrical signals from a conducting layer as a labeled protein 230, 310 passes through a nanopore 255, 330. Non-limiting examples of electrical signals include current, voltage, impedance, capacitance, electromotive force, signal sign, frequency or noise signature measured across a nanopore 255, 330. In some embodiments of the invention, an electrical detector 345 may be operably coupled to one or more conducting layers, a power supply 110 and one or more nanopores 255, 330 penetrating the conducting layers. The detector 345 may comprise an ammeter, voltmeter, capacitance meter and/or conductivity meter, etc. In some embodiments, other electrical components such as resistors or capacitors may be included in the electrical circuit associated with the detector 345.

In various embodiments of the invention, upper 280, 350 and lower 290, 360 chambers may be filled with a low conductivity aqueous buffer. An electrical potential may be applied to conducting layers flanking a nanopore 255, 330. When buffer alone is present, the resistance between the conducting layers is high. The presence of unlabeled regions of proteins 230, 310 passing through the nanopore 255, 330 may produce a slight increase in conductivity across the nanopore 255, 330. The passage of amino acid residues labeled with highly conductive labels 315, such as metal nanoparticles 315, would result in an increase in conductivity that produces a detectable signal at the detector 345. The time interval between detectable electrical signals may be measured and used to create a distance map 140 representing the positions of labeled amino acid residues on the protein 230, 310 molecule for each type of labeled amino acid. The distance map(s) 140 may be used to identify 160 the protein 230, 310 by comparison with known protein 230, 310 sequences. By compiling such maps for each of the twenty types of amino acid residues it would be possible to determine a complete sequence 150 of the protein 230, 310.

Spectrophotometric Detectors

In other embodiments of the invention, amino acid residues labeled with luminescent labels 235, 245 may be detected using an excitatory light source 210 and a photodetector 257 (e.g., Sepaniak et al., J. Microcol. Separations 1:155-157, 1981; Foret et al., Electrophoresis 7:430-432, 1986; Horokawa et al., J. Chromatog. 463:39-49 1989; U.S. Pat. No. 5,302,272.). Exemplary light sources 210 include diode-lasers 210, vertical cavity surface-emitting lasers 210, edge-emitting lasers 210, surface emitting lasers 210 and quantum cavity lasers 210, for example a Continuum Corporation Nd-YAG pumped Ti:Sapphire tunable solid-state laser 210 and a Lambda Physik excimer pumped dye laser 210. Exemplary photodetectors 257 include photodiodes 257, avalanche photodiodes 257, photomultiplier tubes 257, multi-anode photomultiplier tubes 257, phototransistors 257, vacuum photodiodes 257, silicon photodiodes 257, fiber-optic or phototransistor detectors 257 and charge-coupled devices (CCDs) 257. In some embodiments of the invention, an avalanche photodiode (APD) 257 may be used to detect low light levels. The APD process uses photodiode arrays 257 for electron multiplication effects (U.S. Pat. No. 6,197,503).

In some embodiments of the invention, the photodetector 257, light source 210 and nanopore 255, 330 may be fabricated into a semiconductor chip using known N-well Complementary Metal Oxide Semiconductor (CMOS) processes (Orbit Semiconductor, Sunnyvale, Calif.). In alternative embodiments of the invention, the detector 257, light source 210 and nanopore 255, 330 may be fabricated in a silicon-on-insulator CMOS process (e.g., U.S. Pat. No. 6,117,643). In other embodiments of the invention, an array of diode-laser 210 illuminators and CCD detectors 257 may be placed on a semiconductor chip (U.S. Pat. Nos. 4,874,492 and 5,061,067; Eggers et al., BioTechniques 17: 516-524, 1994).

In certain embodiments of the invention, a detector 257 may be positioned perpendicular to a light source 210 to minimize background light. In other embodiments, the light source 210 may be optically separated from the photodetector 257 by one or more light opaque layers 215. Photons generated by excitation of luminescent labels 235, 245 may be collected by a fiber optic and transferred to a CCD detector 257 on a chip (e.g., U.S. Pat. No. 6,274,320). The times at which labeled amino acid residues are detected may be recorded and amino acid residue distance maps 140 may be constructed.

In certain embodiments of the invention, light sources 210, such as light-emitting diodes and/or semiconductor lasers 210 may be incorporated into semiconductor chips (U.S. Pat. No. 6,197,503). Diffractive optical elements that shape a laser 210 or diode light beam may also be integrated into a chip. In some embodiments of the invention, an air-cooled argon laser 210 at 488 nm may excite fluorescein-labeled proteins 230, 310. Emitted light may be collected by an optics system comprising a fiber optic, a lens, an imaging spectrometer, and a 0° C. thermoelectrically-cooled CCD camera 257. Alternative examples of luminescence detectors 257 are known in the art (e.g., U.S. Pat. No. 5,143,8545).

Raman Spectroscopy

In some embodiments of the invention, labeled amino acid residues may be detected by Raman spectroscopy. Raman labels 235, 245, 315 of use in spectrophotometric detection are well known in the art (e.g., U.S. Pat. Nos. 5,306,403; 6,002,471; 6,174,677). Labeled amino acid residues may be excited with a laser 210, photodiode 210, or other light source 210 and the excited amino acid residue detected by a variety of Raman techniques, including but not limited to surface enhanced Raman spectroscopy (SERS), surface enhanced resonance Raman spectroscopy (SERRS) normal Raman scattering, resonance Raman scattering, coherent anti-Stokes Raman spectroscopy (CARS), stimulated Raman scattering, inverse Raman spectroscopy, stimulated gain Raman spectroscopy, hyper-Raman scattering, molecular optical laser 210 examiner (MOLE) or Raman microprobe or Raman microscopy or confocal Raman microspectrometry, three-dimensional or scanning Raman, Raman saturation spectroscopy, time resolved resonance Raman, Raman decoupling spectroscopy or UV-Raman microscopy. In SERS and SERRS, the sensitivity of the Raman detection is enhanced by a factor of $10^6$ or more for molecules adsorbed on roughened metal surfaces, such as silver, gold, platinum, copper or aluminum surfaces. For such embodiments, portions of the nanopores 255, 330 and/or sensor layers 212, 323 may be coated with a Raman sensitive metal, such as silver or gold to provide an enhanced Raman signal.

FRET Detection

In certain alternative embodiments of the invention, a protein 230, 310 may be identified 160 or sequenced 150 using fluorescence resonance energy transfer (FRET). FRET is a spectroscopic phenomenon used to detect proximity between fluorescent donor and acceptor molecules. The donor and acceptor pairs are chosen such that fluorescent emission from the donor overlaps the excitation spectrum of the acceptor. When the two molecules are associated at a distance of less than 100 Angstroms, the excited-state energy of the donor is transferred non-radiatively to the acceptor and the donor emission is quenched. If the acceptor molecule is a fluorophore then its emission is enhanced. Compositions and methods for use of FRET are known (e.g., U.S. Pat. No. 5,866,366).

In certain embodiments of the invention, the donor fluorophore molecules 235, 245 may be attached to an amino acid residue, and the acceptor fluorophore molecules may be connected to a nanopore 255, 330 or sensor layer. Following excitation by a light source 210, the donor fluorophore molecules 234, 245 will transfer their energy to the acceptor molecules, resulting in an enhanced fluorescent signal from the acceptor molecules that may be detected by a photodetector 257.

EXAMPLES

Example 1

Apparatus for Protein Identification and/or Sequencing

Particular embodiments of the invention concerning methods and apparatus 100 for protein 230, 310 identification 160 and/or sequencing 150 are illustrated in FIG. 2 and FIG. 3. The apparatus 100 may comprise one or more sub-devices 200, 300. Each sub-device 200, 300 may comprise fluid filled upper 280, 350 and lower 290, 360 chambers, separated by sensor layers 212, 323. One or more nanopores 255, 330 may extend through the sensor layers 212, 323 and allow passage of labeled proteins 230, 310. The nanopores 255, 330 may be operably coupled to one or more detectors 257, 345 that can detect labeled amino acid residues as they pass through the nanopores 255, 330. In some embodiments of the invention, electrodes 262, 264, 350, 355 in the upper and lower chambers 280, 350, 290, 360 generate an electrical field that drives labeled proteins 230, 310 from the upper 280, 350 to the lower chamber 290, 360 through the nanopores 255, 330. The electrical gradient may be controlled by a voltage regulator 260, 335, which may be operably coupled to a computer 130, 265, 340.

Sensor Layer Construction

In certain embodiments of the invention, illustrated in FIG. 3, photolithography may be used to create an array of multi-planer structures (0.5×0.5 μm) on a silicon substrate, each structure with a silicon base support and one or more layers of gold film or other conductive layers 327 separated by one or more insulator layers 325 comprising, for example, silicon oxide. Other insulator layers 325 overlay the top and bottom conducting layers 327 and insulate the sensor layers 323 from the medium in the upper 350 and lower 360 chambers. Conducting and insulating layers 325, 327 may be formed on a chip by standard semiconductor technologies.

A chip containing the multiplanar structures may be divided into two or more parts. A layer of resist may be coated on the sides of each chip part, perpendicular to the conducting and insulating layers. An AFM/STP tip may be used to etch 5-10 nm lines in the resist layer overlaying each structure. Chemical etching may be used to create nano-scale grooves in each of the structures. When the chip parts are aligned and fused together, the grooves form nanopores 255, 330 and/or nanochannels 255, 330 which extend through the sensor layers 212, 323. Nanowires connecting the conducting layers 327 to electrical detectors 345 may be formed by known methods discussed above. The nanowires may be used to apply a voltage across the conducting layers 327. Changes in current, resistance and/or other electrical properties may be detected with the passage of a protein 230, 310 labeled with electrically conductive labels 315, like gold nanoparticles 315, through the nanopore 255, 330. In certain embodiments of the invention, a thin layer of insulating material may be formed on the sides of the divided chip prior to lithography and etching to prevent current flow except through the nanopore 255, 330.

In certain embodiments of the invention, illustrated in FIG. 2, the sensor layers 212 may comprise one or more light opaque layers 215 and photon sensing layers 220, overlaying a support layer 225. Such embodiments are of use for methods involving photodetection of amino acid residues tagged with luminescent labels 235. The light opaque layers may be formed of any known light opaque material, for example a thin layer of chrome, silver or gold metal. Similarly, photon sensing layers 220 may be comprised of any material that is relatively translucent at the wavelengths of light emitted by the luminescent label 235, for example glass, silicon or certain types of plastics.

In some embodiments of the invention, polymeric materials may be coated on the chip to enhance signal detection. Such polymeric materials may include, but are not limited to, polymethylmethacrylate, ultraviolet-curable polyurethanes and epoxies, and other polymers that exhibit optical transparency, low fluorescence at excitation wavelengths, electrical conductivity and/or insulation. Such materials may be formed into appropriate structures, for example by polymer casting and chemical or photochemical curing (Kim et al., Nature 376: 581-584 1995).

Example 2

Photodetection

In embodiments of the invention involving photodetection (FIG. 2), amino acid residues labeled with a luminescent label 235 may be excited by a light source 210, such as a laser 210. Excitatory light may pass through a transparent window 240 in the upper chamber 280, exciting the luminescent label 235 to a higher energy state. The labeled amino acid passes through the light opaque layer 215, cutting off the source 210 of excitatory light and shielding the photodetector 257 from the light source 210. As the luminescent label 235 passes the photon sensing layer 220, it emits a photon and becomes quenched 245. The emitted photon may be detected by a photodetector 257. The detected signal may be amplified by an amplifier 270 and stored and/or processed by a computer 265. The computer 265 may also record the time at which each labeled amino acid passes through the nanopore 255, allowing the calculation of distances between adjacent labeled amino acid residues and the compilation of a distance map 140 for each type of labeled amino acid.

In certain embodiments of the invention, a highly sensitive cooled CCD detector 257 may be used. The cooled CCD detector 257 has a probability of single-photon detection of up to 80%, a high spatial resolution pixel size (5 microns), and sensitivity in the visible through near infrared spectra. (Sheppard, Confocal Microscopy: Basic Principles and System Performance in: Multidimensional Microscopy, Cheng et al. Eds., Springer-Verlag, New York, N.Y. pp. 1-51, 1994.) In another embodiment of the invention, a coiled image-intensified coupling device (ICCD) may be used as a photodetector 257 that approaches single-photon counting levels (U.S. Pat. No. 6,147,198). A nanochannel plate operates as photomultiplier tube wherein a small number of photons triggers an avalanche of electrons that impinge on a phosphor screen, producing an illuminated image. This phosphor image is sensed by a CCD chip region 257 attached to an amplifier 270 through a fiber optic coupler. In some embodiments of the invention, a CCD detector 257 on the chip may be sensitive to ultraviolet, visible, and/or infrared spectra light (U.S. Pat. No. 5,846,708).

Example 3

Electrical Detection

In other embodiments of the invention (FIG. 3), amino acid residues may be labeled with a label 315 that can be detected by its electrical properties. In one non-limiting example, the label 315 may comprise gold nanoparticles 315. As an amino acid residue labeled with a gold nanoparticle 315 passes through a nanopore 330, it produces detectable changes in the conductivity, resistance and other electrical properties of the nanopore 330. The conducting layers 327 flanking a nanopore 330 may be operably coupled to an electrical detector 345, which may detect any type of electrical signal, such as voltage, conductivity, capacitance, etc. The detector 345 may be operably coupled to a computer 340 to process and store data. Distance maps 140 showing distances between labeled amino acid residues may be constructed and used to identify 160 and/or sequence 150 the labeled protein.

In particular embodiments of the invention, 2 to 5 nm nanopores 330 may provide fluid communication between the upper 350 and lower 360 chambers. Proteins 310 labeled with 1 nm gold nanoparticles 315 may be synthesized and/or placed in the upper chamber 350. An electrical detector 345, such as a voltage detector 345, and power supply 110 may be operably coupled to conducting layers 327 flanking the nanopore 330. Current across the nanopore 330 may be converted to voltage and amplified using an AxopatchA (Axon Instruments, Foster City, Calif.) or a Dagan 3900A patch clamp amplifier 270 (Dagan Instruments, Minneapolis, Minn.). The signal may be filtered using a Frequency Devices (Haverhill, Mass.) low pass Bessel filter. Data may be digitized using a National Instruments (Austin, Tex.) AT-MIO-16-X 16-bit board and LAB WINDOWS/CVI programs. The chip may be shielded from electric and magnetic noise sources using a mu-metal box (Amuneal, Philadelphia, Pa.) (see Kasianowicz, et al., 1996).

All of the METHODS and APPARATUS 100 disclosed and claimed herein can be made and executed without undue experimentation in light of the present disclosure. It will be apparent to those of skill in the art that variations may be applied to the METHODS and APPARATUS 100 described herein without departing from the concept, spirit and scope of the claimed subject matter. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the claimed subject matter.

What is claimed is:

1. An apparatus comprising:
   a) at least one sub-device, each sub-device comprising a first chamber and a second chamber, said first and second chambers separated by sensor layers comprising a semiconductor material and having one or more nanopores therein, the first and second chambers of each sub-device in fluid communication through said one or more nanopores, wherein said nanopores are between 1 and 999 nm in diameter; and b) one or more detectors comprising said sensor layers and configured to detect one or more analytes in the nanopores passing from said first chamber to said second chamber.

2. The apparatus of claim 1, further comprising an electrode in each first and second chambers, said electrodes operably coupled to a voltage regulator.

3. The apparatus of claim 1, further comprising a computer operably coupled to the one or more detectors.

4. The apparatus of claim 1, wherein the one or more detectors further comprise a photodetector, an electrical detector and/or a voltage detector.

5. The apparatus of claim 1, wherein said sensor layers comprise a support layer, a photon sensing layer and a light opaque layer.

6. The apparatus of claim 5, wherein said photon sensing layer is operably coupled to one or more photodetectors.

7. The apparatus of claim 6, further comprising a light source and an amplifier.

8. The apparatus of claim 1, wherein said sensor layers comprise at least one conducting layer and at least two insulating layers.

9. The apparatus of claim 8, wherein said conducting layer is operably coupled to one or more electrical detectors.

10. The apparatus of claim 1, wherein said nanopore is part of a nanotube or nanochannel.

11. The apparatus of claim 2, further comprising a computer operably coupled to said voltage regulator.

12. An apparatus comprising:
a first chamber;
a second chamber;
sensor layers separating said first and second chambers, said sensor layers comprising a semiconductor material and including one or more nanopores extending through said sensor layers, said first and second chambers being in fluid communication through said one or more nanopores, wherein said nanopores are between 1 and 999 nm in diameter; and
one or more detectors comprising said sensor layers operably coupled to said sensor layers and configured to detect one or more analytes in the nanopores passing from said first chamber to said second chamber.

13. The apparatus of claim 12, wherein said one or more detectors further comprise a photodetector, an electrical detector and/or a voltage detector.

14. The apparatus of claim 12, further comprising a computer operably coupled to said one or more detectors.

15. The apparatus of claim 12, further comprising:
an electrode in each upper and lower chamber, and a voltage regulator operably coupled to said electrodes.

16. The apparatus of claim 12, wherein said sensor layers comprise a support layer, a photon sensing layer and a light opaque layer.

17. The apparatus of claim 16, wherein said photon sensing layer is operably coupled to one or more photodetectors.

18. The apparatus of claim 12, wherein said sensor layers comprise at least one conducting layer and at least two insulating layers.

19. The apparatus of claim 18, wherein said conducting layer is operably coupled to one or more electrical detectors.

20. The apparatus of claim 12, wherein said nanopores and/or sensor layers are coated with a Raman sensitive metal.

21. The apparatus of claim 12, wherein said nanopores comprise single ion channels.

22. An apparatus comprising:
one or more first chambers in fluid communication with one or more second chambers via one or more nanopores, said one or more first chambers and said one or more second chambers separated by sensor layers comprising a semiconductor material and having said one or more nanopores therein, wherein said nanopores are between 1 and 999 nm in diameter; and
one or more detectors comprising said sensor layers and configured to detect one or more analytes in the nanopores passing from said first chamber to said second chamber.

23. The apparatus of claim 22, further comprising a computer operably coupled to said-one or more detectors.

24. The apparatus of claim 22, further comprising:
an electrode in each first and second chambers, and a voltage regulator operably coupled to said electrodes.

25. The apparatus of claim 12, further comprising an electrode in each first and second chambers, said electrodes operably coupled to a voltage regulator.

26. The apparatus of claim 1, further comprising a light source, wherein the one or more nanopores, the one or more detectors, and the light source are integrated on a single chip.

27. The apparatus of claim 12, further comprising a light source, wherein the one or more nanopores, the one or more detectors, and the light source are integrated on a single chip.

28. The apparatus of claim 22, further comprising a light source, wherein the one or more nanopores, the one or more detectors, and the light source are integrated on a single chip.

29. The apparatus of claim 1, wherein the one or more nanopores and the one or more detectors are incorporated into one or more micro-electro-mechanical systems.

30. The apparatus of claim 12, wherein the one or more nanopores and the one or more detectors are incorporated into one or more micro-electro-mechanical systems.

31. The apparatus of claim 22, wherein the one or more nanopores and the one or more detectors are incorporated into one or more micro-electro-mechanical systems.

32. The apparatus of claim 1, wherein the semiconductor material is selected from the group consisting of silicon, silicon nitride, germanium, gallium arsenide, a metal and a metal oxide.

33. The apparatus of claim 12, wherein the semiconductor material is selected from the group consisting of silicon, silicon nitride, germanium, gallium arsenide, a metal and a metal oxide.

34. The apparatus of claim 22, wherein the semiconductor material is selected from the group consisting of silicon, silicon nitride, germanium, gallium arsenide, a metal and a metal oxide.

* * * * *